US006234025B1

United States Patent
Gieske et al.

(10) Patent No.: US 6,234,025 B1
(45) Date of Patent: May 22, 2001

(54) ULTRASONIC INSPECTION APPARATUS AND METHOD USING A FOCUSED WAVE DEVICE

(75) Inventors: John H. Gieske; Dennis P. Roach; Phillip D. Walkington, all of Albuquerque, NM (US)

(73) Assignee: Sandia Corporation, Albuquerque, NM (US)

(*) Notice: Subject to any disclaimer, the term of this patent is extended or adjusted under 35 U.S.C. 154(b) by 0 days.

(21) Appl. No.: 09/280,411

(22) Filed: Mar. 29, 1999

(51) Int. Cl.[7] .................................................. G01N 29/10
(52) U.S. Cl. .................................................. 73/642; 73/629
(58) Field of Search .......................... 73/642, 644, 629; 310/335, 336

(56) References Cited

U.S. PATENT DOCUMENTS 4,183,249 * 1/1980 Anderson ............................... 73/642
5,060,201 * 10/1991 Ishikawa et al. ...................... 73/642
5,343,109 * 8/1994 Mockl .................................... 73/644

OTHER PUBLICATIONS

J. H. Gieske, et al., "Ultrasonic Inspection Technique for Composite Doubler/Aluminum Skin Bond Integrity for Aircraft", 8 pp (published Apr. 2, 1998.

D. P. Roach, et al, "Development and Validation of Nondestructive Inspection Techniques for Composite Doubler Repairs on Commercial Aircraft", Sandia National Laboratories, Albuquerque NM Sandia Report SAND 98–1014UC906 (published May 1, 1998.

* cited by examiner

Primary Examiner—John E. Chapman
(74) Attorney, Agent, or Firm—Russell D. Elliott

(57) ABSTRACT

An ultrasonic pulse echo inspection apparatus and method for detecting structural failures. A focus lens is coupled to the transducer to focus the ultrasonic signal on an area to be inspected and a stop is placed in the focus lens to block selected ultrasonic waves. Other waves are not blocked and are transmitted through the structure to arrive at interfaces therein concurrently to produce an echo response with significantly less distortion.

23 Claims, 14 Drawing Sheets

ULTRASONIC INSPECTION APPARATUS AND METHOD USING A FOCUSED WAVE DEVICE

GOVERNMENT RIGHTS

The Government has rights to this invention pursuant to Contract No. DE-AC04-94AL85000 awarded by the U.S. Department of Energy.

BACKGROUND OF THE INVENTION

1. Field of the Invention (Technical Field)

The present invention relates to ultrasonic inspection of structural failures particularly for detecting disbonds or delaminations.

2. Background Art

One of the primary goals of the Federal Aviation Administration's (FAA) National Aging Aircraft Research Program (NAARP) is to foster new technology associated with the repair of civil aircraft. A typical aircraft can experience over 2,000 fatigue cycles (cabin pressurizations) and many more flight hours in a single year. The unavoidable by-product of this use is that flaws develop throughout the aircraft's skin and substructure elements. These flaws can take the form of cracks, corrosion, disbonds, dents, and gouges.

Composite doublers, or repair patches, provide a repair technique that can enhance the way aircraft are maintained. The high modulus of Boron-Epoxy composite material enables a doubler to pick up load efficiently and effectively when bonded to a metal structure. The load transfer occurs by shear through the adhesive. The composite doubler repair has several advantages over conventional repairs which include: corrosion resistance; light weight/high strength; elimination of rivets and additional rivet holes in the skin; conformation to complex shapes; access only to the outside of the fuselage being needed; and substantial cost and time savings.

As the commercial airline industry responds to calls for the ensured airworthiness of global airline fleets, inspection reliability is of growing importance. The development and application of new Nondestructive Inspection (NDI) techniques needs to keep pace with the growing understanding of aircraft structural aging phenomena. A primary inspection requirement for these doublers is the identification of disbonds between the composite laminate and the aluminum parent material.

Acceptance of composite doublers by civil aviation industry depends highly on a quick and comprehensive assessment of the integrity of the doubler at the initial installation of the composite doubler and at regular inspection intervals of the aircraft. In particular, identification of disbonds between the doubler and the aluminum skin and delaminations within the composite are important since these defects prevent the doubler from performing as designed. Disbonds can occur at installation of the doubler or at anytime during the service life of the aircraft. Because of the rapidly increasing use of composites on commercial airplanes, coupled with the potential for economic savings associated with their use in aircraft structures, it appears that the demand for validated composite inspection techniques will increase.

The two main potential causes of structural failure in composite doubler installations are cracks in the aluminum and adhesive disbonds/delaminations. When disbonds or delaminations occur, they may lead to joint failures. By their nature, they occur at an interface and are, therefore, always hidden. A combination of fatigue loads and other environmental weathering effects can combine to initiate these types of flaws. Periodic inspections of the composite doubler for disbonds and delaminations (from fabrication, installation, fatigue, or impact damage) is essential to assuring.the successful operation of the doubler over time. The interactions at the bond interface are extremely complex, with the result that the strength of the bond is difficult to predict or measure. Even a partial disbond may compromise the integrity of the structural assembly. Therefore, it is necessary to detect all areas of disbonding or delamination before joint failures can occur.

Ultrasonic inspection is a nondestructive method in which beams of high frequency sound waves are introduced into materials for the detection of surface and subsurface flaws in the material. In ultrasonic pulse-echo inspections, short bursts of ultrasonic energy are interjected into a testpiece at regular intervals of time. In most pulse-echo systems, a single transducer acts alternately as the sending and receiving transducer. Sometimes it is advantageous to use separate sending and receiving transducers for pulse-echo inspection. The term pitch-catch is often used in connection with separate sending and receiving transducers.

The sound waves, normally at frequencies between 0.1 and 25 MHz, travel through the material with some attendant loss of energy (attenuation) and are reflected at interfaces. The reflected beam is displayed and then analyzed to define the presence and location of flaws. The degree of reflection depends largely on the physical state of the materials forming the interface. Cracks, delaminations, shrinkage cavities, pores, disbonds, and other discontinuities that produce reflective interfaces can be detected. Complete reflection, partial reflection, scattering or other detectable effect on the ultrasonic waves can be used as the basis of flaw detection. In addition to wave reflection, other variations in the wave, which can be monitored, include: time of transit through the structure to be inspected, attenuation, and features of the spectral response.

The principal advantages of ultrasonic inspection as compared to other NDI techniques are: superior penetrating power for detection of deep flaws; high sensitivity permitting the detection of extremely small flaws; accuracy in determining size and position of flaws; only one surface need be accessible; nonhazardous operations with no effect on personnel and equipment nearby; portability; and output that can be digitally processed. However, conventional pulse-echo techniques using flat or normal focus transducers are not effective in characterizing the disbond condition of a composite/aluminum interface. For example, when using 2" diameter focus transducers, the echo amplitude change observed at the disbond may be only slightly different than that due to unflawed portions of the composite bond-line.

The present invention overcomes these difficulties encountered with prior art flat transducer ultrasonics inspection. In the preferred embodiment, a noticeable improvement in the pulse echo response can be obtained by using a transducer with a focus-lens and by placing a stop in the center of the transducer. A discussion of this technology is included in the article entitled "Ultrasonic Inspection Technique for Composite Doubler/Aluminum Skin Bond Integrity for Aircraft," authored by J. Gieske, D. Roach, and P. Walkington, and also in Sandia Report SAND98-1014, UC 906 entitled "Development and Validation of Nondestructive Inspection Techniques for Composite Doubler Repairs on Commercial Aircraft," authored by D. Roach and P. Walkington, and the disclosures therein are herein incorporated by reference.

SUMMARY OF THE INVENTION

DISCLOSURE OF THE INVENTION

The present invention is an apparatus and method for improving conventional ultrasonic inspections of structures. In the preferred embodiment, a transducer is used to create an ultrasonic signal and a stop is oriented to block selected waves of the ultrasonic signal. Most preferably a focus lens is used to focus the ultrasonic signal upon the desired area of the structure to be inspected. A scanning system is used to control the transducer and collect reflected ultrasonic data from the transducer. A couplant, such as water, is used to aid in coupling the ultrasonic signal between the transducer and structure. A scanning shoe can be used to increase the distance traveled by the ultrasonic signal. The ultrasonic transducer preferably has a diameter of at least approximately 0.5 inches, and most preferably of approximately 1.0 inch, and operates between approximately 0.1 and 25 megahertz, most preferably five megahertz. The focus lens is conductive and refractive of ultrasonic waves and defines a radius of curvature such that signal waves transmitted by the transducer are focused upon a selected area of the structure. The stop is preferably an ultrasonic-attenuating material, such as cork, and has a diameter such that selected L-waves transmitted by the transducer through the structure are blocked by the stop. The stop is preferably a cylindrical cork button having a diameter of approximately 0.5 inches and a thickness of approximately 0.25 inches. The entire apparatus can comprise at least one transducer for transmitting ultrasonic signals and receiving reflected ultrasonic signals, a lens coupled to the transducer(s), a stop coupled to the lens, a scanning system housing the transducer(s), a scanner shoe coupled to the transducer(s) for increasing the distance traveled by the transmitted ultrasonic signal, a couplant between the transducer(s) and the structure, and an electronic depth gate in the scanning system for selecting certain of the reflected ultrasonic signals.

The method of inspecting a structure with ultrasonic signals most preferably involves coupling a transducer output to the structure, blocking selected L-wave components of the ultrasonic signal from the transducer output, transmitting selected L-wave components of the ultrasonic signal from the transducer output through the structure, and receiving the reflected ultrasonic signal from the structure. The method can further comprise the step of focusing the ultrasonic signal from the transducer upon a selected area of the structure to be inspected. The method can include increasing the distance traveled by the ultrasonic signal between the transducer and structure. An image of the received ultrasonic signal can be produced revealing defects within the structure. Gating the image to reveal the reflected ultrasonic signal at selected depths further improves the image.

A primary object of the present invention is to improve the sensitivity of ultrasonic pulse echo inspections.

A primary advantage of the present invention is the improved sensitivity of conventional A-scans and C-scans using ultrasonic pulse echo techniques for the inspection of structures.

Another advantage of the present invention is the ability to detect disbonds and delaminations in composite doublers used to repair aluminum surfaces due to improved sensitivity at structure interfaces.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS

BEST MODES FOR CARRYING OUT THE INVENTION

Figure 1:
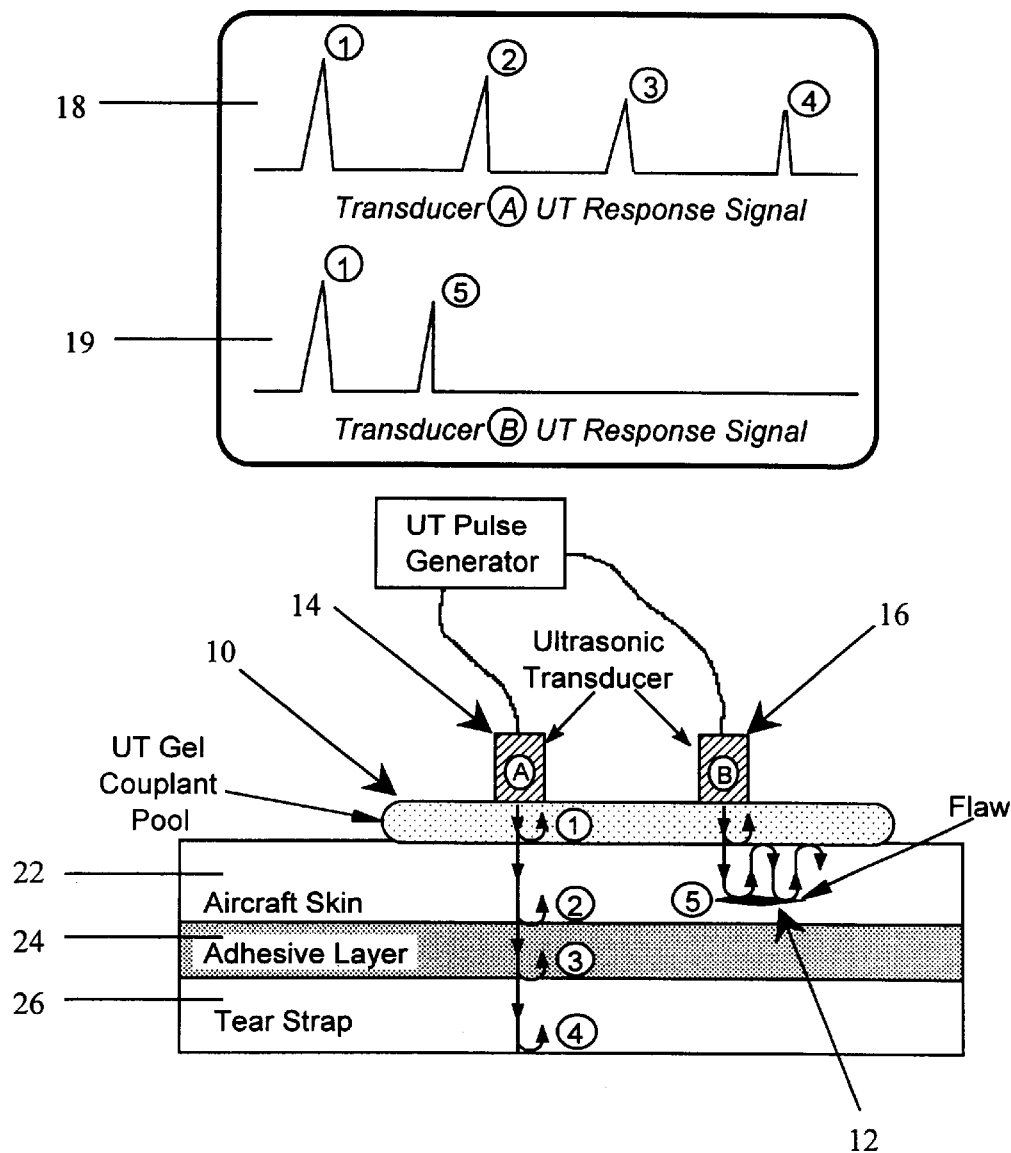
FIG. 1 is a diagram demonstrating the basic operation of ultrasonic pulse echo inspection.

FIG. 1 is a diagram demonstrating the pulse-echo technique of the present invention and the interaction of ultrasonic waves with the various interfaces within a structure. Layers 22, 24, and 26 can represent, for example, an aircraft skin, an adhesive layer, and a tear strap respectively. The mechanical vibration, or ultrasonic pulse—for example on the order of five megahertz—is introduced into a portion of the structure to be inspected through couplant 10, which can be an ultrasonic gel couplant pool or water, and travels by wave motion through the structure to be inspected at the velocity of sound, which depends on the material. If the pulses encounter a reflecting surface, some or all of the energy is reflected and monitored by the transducer. The reflected beam, or echo, can be created by any normal (e.g., in multilayered structures) or abnormal (flaw) interface. Two transducers are shown to demonstrate the difference between a normal structure and a flawed structure. A first ultrasonic transducer 14 sends and receives a signal, the response of which is shown on plot 18. A second ultrasonic transducer 16 sends and receives a signal, the response of which is shown on plot 20. Because the signal from second transducer 16 encounters flaw 12, the signal is reflected back and therefore plot 20 is quite different from the "normal" plot 18 from first transducer 14. Plots 18 and 20 are typical "A-scan" plots of pulse echo responses.

In the case of disbond and delamination inspections, it is sometimes difficult to clearly identify flaws using A-Scan signals alone. Small porosity pockets commonly found in composites, coupled with signal fluctuations caused by material nonuniformities can create signal interpretation difficulties. These inspection impediments are primarily troublesome in thicker composite laminates, which exceed twenty plies. Significant improvements in disbond and delamination detection can be achieved by taking A-Scan signals and transforming them into a single C-Scan image of the part being inspected. C-Scan uses information from single point A-Scan waveforms to produce an area mapping of the inspection surface. These two-dimensional ("2-D") images are produced by digitizing point-by-point signal variations of an interrogating sensor while it is scanned over a surface. C-Scan area views provide the inspector with easier-to-use and more reliable data with which to recognize flaw patterns. This format provides a quantitative display of signal amplitudes or time-of-flight data can be converted and displayed by image processing-equipment to provide an indication of flaw depth. A variety of PC-based manual and automated scanning devices can provide position information with digitized ultrasonic signals. Specific emphasis can be placed on portions of the ultrasonic signal and highlighted in the color-mapping C-Scan based on user-specified amplitude gates, time-of-flight values and signal waveforms.

Figure 2:
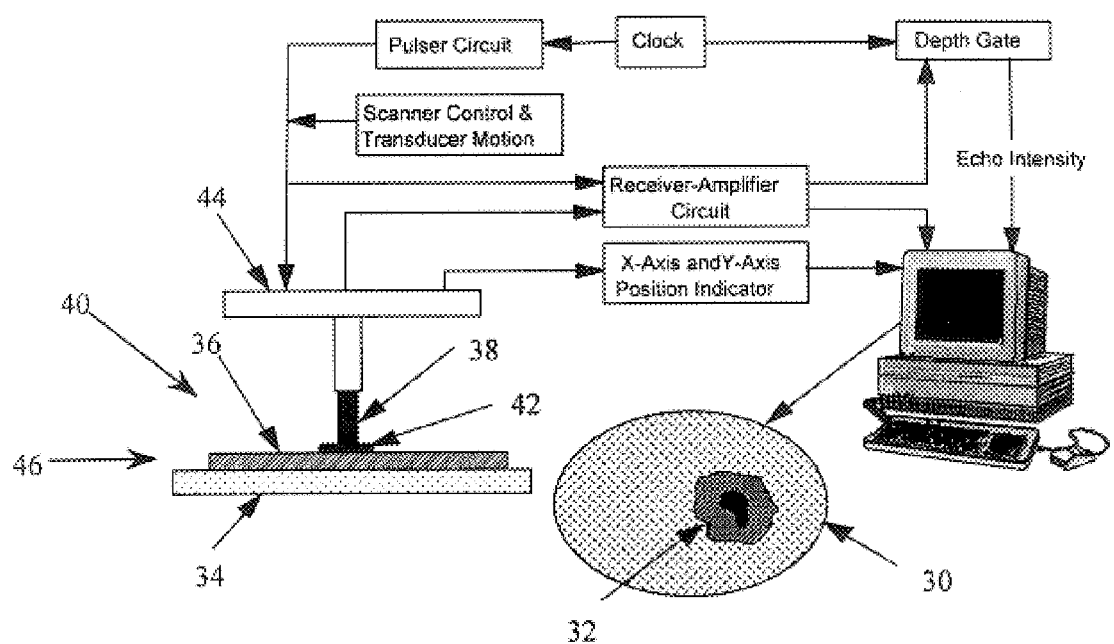
FIG. 2 is a diagram demonstrating the basic operation of an ultrasonic C-scan imaging system used in accordance with the present invention.

The basic C-Scan system used in the present invention to inspect, for example, bonded composite doublers, is shown diagrammatically in FIG. 2. Scanning unit 40 containing transducer 38 is moved over the surface of structure 46 to be inspected which is comprised of, for example, composite doubler 36 and aluminum substrate 34, using a search pattern of closely spaced parallel lines. Coupler 42, such as a water or gel pool, couples transducer 38 to structure 46. X-Y mechanical linkage 44 connects scanning unit 40 to X-axis and Y-axis position indicators, which feed position data to a computer. The echo signal is recorded, versus its X-Y position on structure 46, and color coded image 30 is produced from the relative characteristics of the sum total of signals received. Flaw 32 is revealed upon image 30. One scanner system that can be used for such an inspection is the "Ultra Image IV" manufactured by SAIC/Ultra Image Inc.

Figure 3:
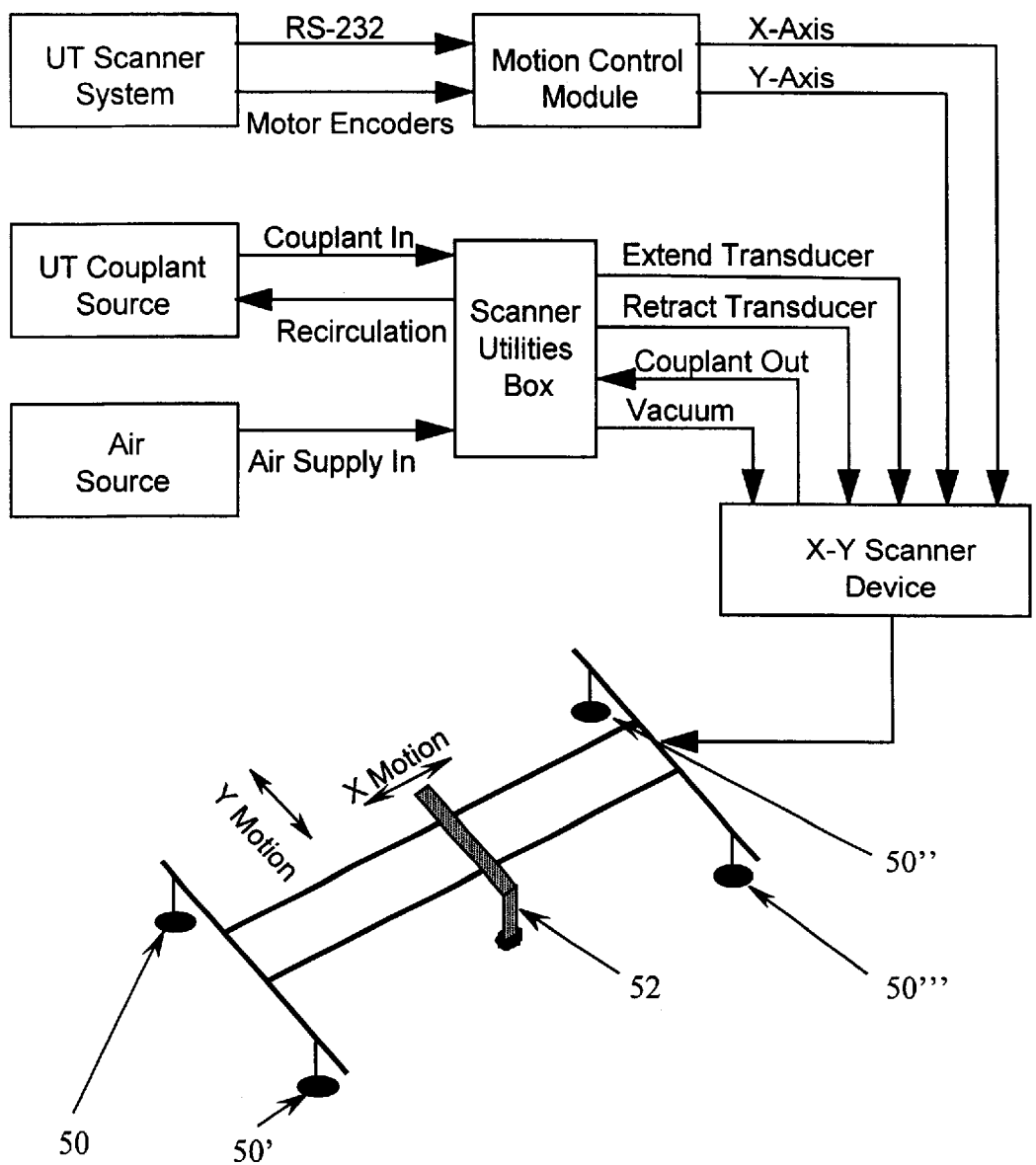
FIG. 3 is a scanning device interconnection diagram used in accordance with the present invention.
Figure 4:
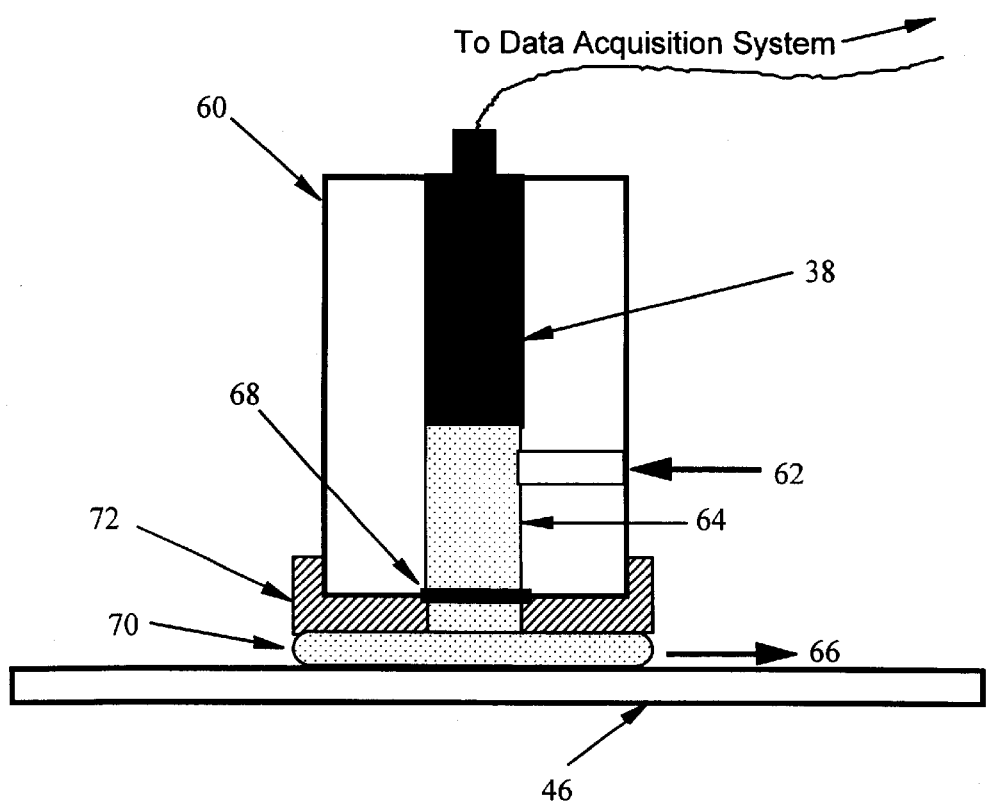
FIG. 4 is a diagram of the transducer assembly used in accordance with the present invention.

FIG. 3 shows the preferred Ultra Image IV interconnection diagram used in accordance with the present invention. This set-up is typical for most scanner devices. Both manual and automated (motorized) scanners are available. Suction cups 50, 50', 50", and 50''' maintain contact with the structure to be inspected, and transducer extend and retract mechanism 52 further moves the transducer. FIG. 4 shows in more detail the transducer assembly of the present invention. Ultrasonic transducer 38 communicates with a data acquisition system, or computer. Water is used as the couplant, and water inlet 62 brings water from a reservoir and is captured as a water column 64 for coupling. Weeper body 60 is a cylinder which holds water column 64. Weeper plastic membrane 68 is pierced to provide water flow to structure 46. Water pool 70 forms beneath membrane 68. Scanning shoe 72, which can be made of plastic, helps the transducer system slide along wetted structure 46 and provides additional offset of the ultrasonic wave. Scanning shoe 72 increases the distance traveled by the ultrasonic signal thus offsetting the peaks caused by interaction of the ultrasonic wave with certain interfaces such as weeper plastic membrane 68 and structure 46 front surface. This makes it easier to establish the initial interface pulse, or echo, from the inspection surface which is essential in setting up the C-scan gates discussed below. The degree of peak offset can be further controlled, for example, by the thickness of a rubber-impregnated cloth washer placed inside the scanning shoe 72. Excess water flow is recovered at 66 into the water reservoir.

Another aspect of a successful inspection is the positioning of a series of gates corresponding to specific thicknesses of the material to be inspected. An electronic depth gate is an element in C-scan systems. The gates operate on the A-scan signals received during an inspection and allow users to focus on specific phenomenon in particular time frames (depths) within the structure. User-specified depth gates allow only those echo signals that are received within a limited range of delay times following the initial pulse, or interface echo, to be admitted to the receiver-amplifier circuit. The color coded C-scan reflects these focus areas. Depth gates are adjustable. By setting a depth gate for a specific range of delay times, echo signals from key areas of the test article, parallel to the scanned surface, can be recorded.

In the preferred embodiment of the present invention, the gates are set so that front reflections from the structure being inspected are de-emphasized in the display. In the case of inspecting a composite doubler upon a metal surface, echoes from within the composite doubler and at the metal-to-composite bond interface are emphasized. For such an inspection, three gates can be set to collect: 1) delamination or porosity signals from within the doubler, 2) the bond interface signal, and 3) the metal, such as aluminum, back-surface echo.

Figure 5:
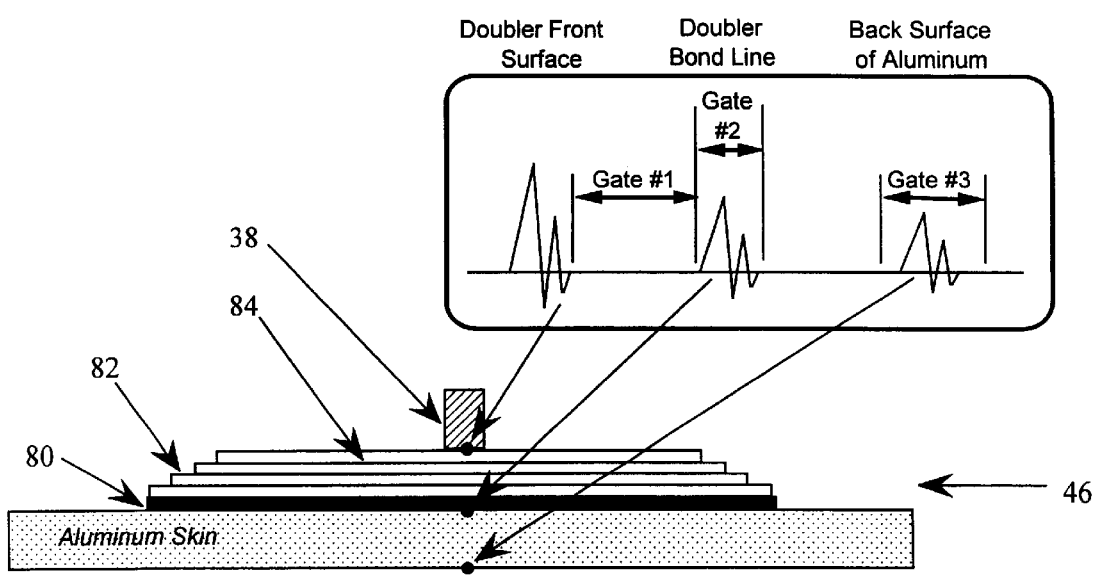
FIG. 5 is a diagram showing ultrasonic wave peaks produced at structure interfaces and the time delay locations of three corresponding gates of the data acquisition system used in accordance with the present invention.

FIG. 5 is a diagram showing the various ultrasonic wave peaks produced at interfaces and the time delay locations of three corresponding gates used in accordance with the present invention. As an example structure 46 to be inspected, an aluminum skin is shown having adhesive layer 80 attaching boron-epoxy doubler 84. Tapered edge 82 of doubler 84 is also shown in this figure. Inspection for composite doubler disbonds is particularly important in the tapered region of a repair patch. Ultrasonic transducer 38 is coupled to structure 46. The gates are set such that only the selected interfaces are revealed.

The detection of disbonds at interfaces is quite challenging. When using, for example, 2 inch diameter focus transducers, the echo amplitude change observed at a disbond may be only slightly different than that due to unflawed portions of the composite bond-line. In the preferred embodiment of the present invention, a noticeable improvement in the bond-line echo response at a disbond is obtained by using a focused transducer, for example, a one-inch diameter, two-inch focus transducer. The echo response is further enhanced by placing a stop, for example a 3/8 inch diameter, 3 inch thick cork button, in the center of the transducer.

Figure 6:
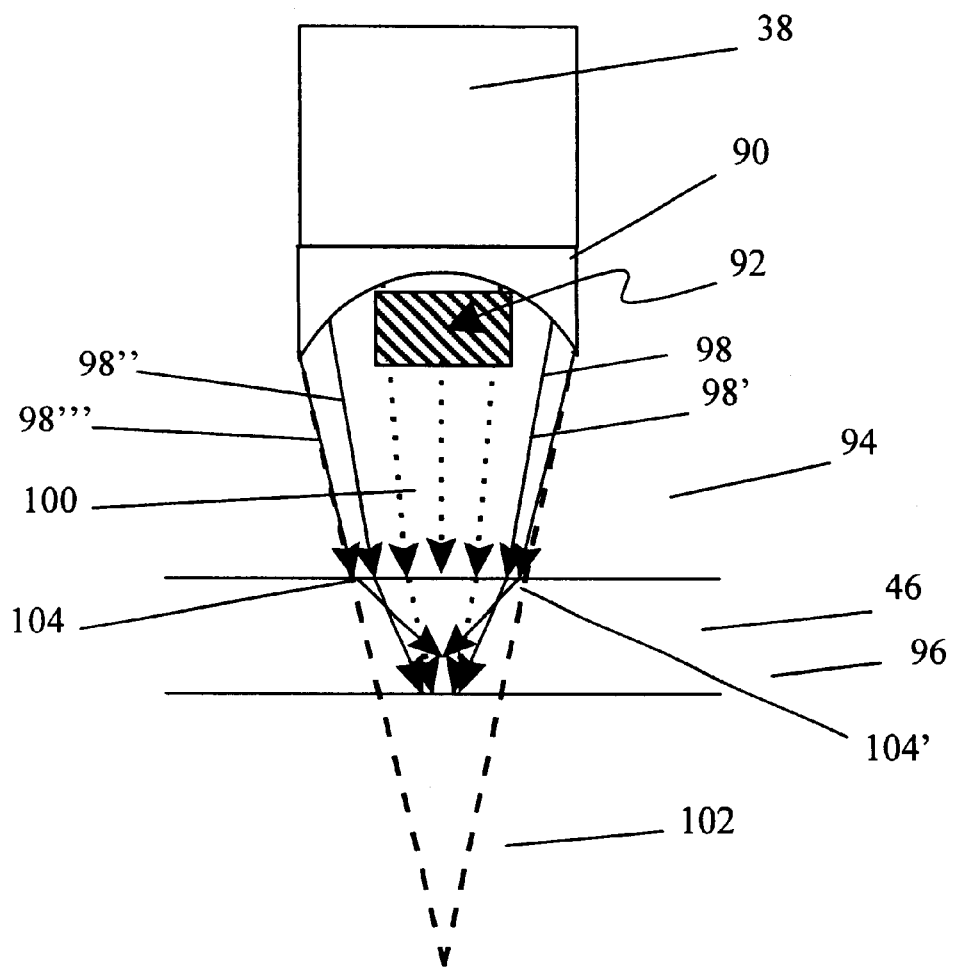
FIG. 6 shows the preferred embodiment of the transducer, focus lens, and stop of the present invention.

The diagram in FIG. 6 shows the preferred embodiment of the transducer apparatus of the present invention. FIG. 6 shows transducer 38, focus lens 90 and stop 92, and demonstrates an example ultrasonic pulse beam path created with this improved transducer apparatus. Focus lens 90 aids in focusing the ultrasonic signal on a selected area of structure 46. Focus lens 90 is constructed of a conductive and refractive material of ultrasonic waves, for example, plastic or glass, and is affixed to transducer 38 by a shoe means. The radius of curvature of focus lens 90 is chosen to focus the selected ultrasonic signal outer rays 98, 98', 98", and 98'" on the area to be inspected. A flat transducer would not focus the signal.

Theoretical rays shown generally at 102 show the focal point of focus lens 90 if stop 92 and structure 46 to be inspected were not present. Ray traces of the ultrasonic pulse beam shown generally at 94, drawn downward from transducer 38, focus on interface 96. The large refracted angles for selected outer rays 98, 98', 98", and 98'" of the ultrasonic beam are due to the elastic anisotropy of the composite material making up structure 46 to be inspected. These angles change significantly from the thickness direction to the transverse direction when structure 46 is composed of a composite material such as a Boron-Epoxy composite doubler. Stop 92 is comprised of a low density material that is highly attenuative of ultrasonic waves, for example cork. Stop 92 effectively blocks selected zero and low-angle ultrasonic waves shown generally at 100 travelling in its path.

This modified transducer apparatus and inspection method shown in FIG. 6 allows the user to focus all the ultrasonic signal energy upon the area of interest to be inspected. Without the improvements offered by the present invention, the ultrasonic waves arrive at different times upon the area of interest and the response data retrieved is distorted. With the improvements of the present invention, the response sensitivity is optimized and distortion is minimized.

Refracted angles shown generally at 104 and 104' in structure 46 are calculated using L-wave velocity values that are measured in a sample of structure 46. Typically, higher L-wave velocity waves have higher angles of refraction, particularly when structure 46 is a Boron-Expoxy composite doubler. L-wave velocity values and the corresponding angles of refraction are measured using known techniques readily available to those skilled in the art.

FIG. 6 shows that by placing stop 92 in the center of transducer 38 and focus lens 90, selected zero and low-angle ultrasonic waves 100 are blocked so that only other selected faster velocity, larger-refracted outer rays 98, 98', 98", and 98'" are transmitted into structure 46. Faster L-wave velocity outer rays 98, 98', 98", and 98'" interact with interface 96 to enhance the difference of the echo response between, for example, bonded and non-bonded conditions of the interface.

Stop 92 is adhered to focus lens 90 with glue or any type adhesive. There are many alternative means by which stop 92 can be placed to block zero and low-angle ultrasonic waves 100 and will be apparent to those skilled in the art. Selected zero and low-angle ultrasonic waves 100 can be blocked up to any angle desired by stop 92 as necessary to perform the inspection at hand by taking into account the type of material which is to be inspected. The focus point of focus lens 90 is of course also adjustable to suit the inspection task and structure to be inspected. Various sizes, shapes, types, and materials of transducer 38, focus lens 90, and stop 92 can be employed in the present invention and these will be apparent to those skilled in the art.

Therefore, the present invention is most preferably an ultrasonic pulse-echo inspection apparatus and method using a modified focus transducer having a stop where a robust signal amplitude signature of an interface is obtained to characterize, for example, the condition of the bond between a composite doubler and aluminum. However, this apparatus and method can be used to inspect for structural failures in many types of materials such as metals, steel, synthetic materials, and composite materials. Many types of structures to be inspected could be examined with the present invention, for example, automobiles and inspections in the petroleum industry. The modified focus transducer is also compatible with portable ultrasonic scanning systems that utilize the weeper or dripless bubbler technologies and is particularly useful for ultrasonic inspection of the boron-epoxy composite doublers installed on aircraft.

Industrial Applicability:

The invention is further illustrated by the following non-limiting example.

EXAMPLE

In this example, the ultrasonic inspection apparatus and inspection method using a modified focus transducer was used to identify disbonds between a composite doubler and the aluminum skin of an aircraft fuselage. A study to assess the performance capabilities of composite doublers was chosen on an L-1011 aircraft for reinforcement of the upper right corner of a cargo doorframe of the fuselage. For this application, a boron-epoxy composite doubler, or repair patch, of 72 plies was installed.

Figure 7:
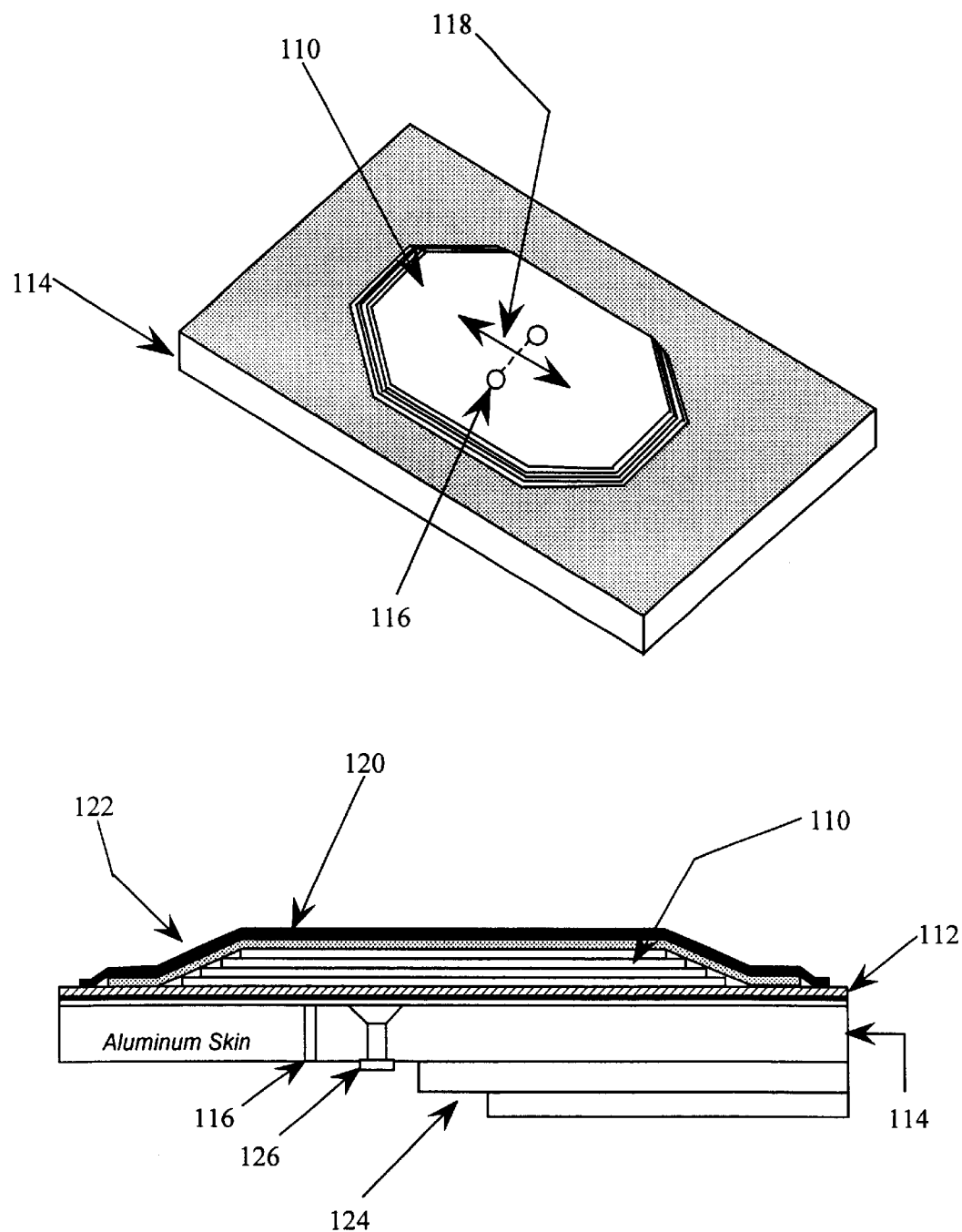
FIG. 7 shows elements of an example composite doubler to be inspected.

The elements of the Boron-Epoxy composite doubler are shown in FIG. 7 where the thickness dimensions are greatly exaggerated to illustrate the lay-up construction of the composite. The aluminum skins where the doublers are normally installed range in thickness from 0.04 to 0.07 inch. A typical application of a composite doubler or repair patch is shown for the case of a fatigue crack repair. Aluminum skin 114 is connected to boron-epoxy doubler 110 by adhesive layer 112. Structural damage 116, for example a stop-drilled crack, is shown in aluminum skin 114 next to rivet 126. Tapered region 122 of doubler 110 is also illustrated. Tapered region 122 near the perimeter of doubler 110 as shown in FIG. 7 is necessary to achieve a uniform stress field in the area of maximum load transition. Doubler 110 is covered by fiberglass cover ply 120. Substructure elements 124 are also shown, which can be for example, a stringer and tear strap. Applied stress 118 is shown next to structural damage 116.

The number of plies and fiber orientation of the composite is determined by the nature of the reinforcement required. For the application of the doubler at the L-1011 cargo door frame, a boron-epoxy composite of 72 plies was required where alternate ply orientations of 0, 90, and +/−45 degrees were used.

Figure 8:
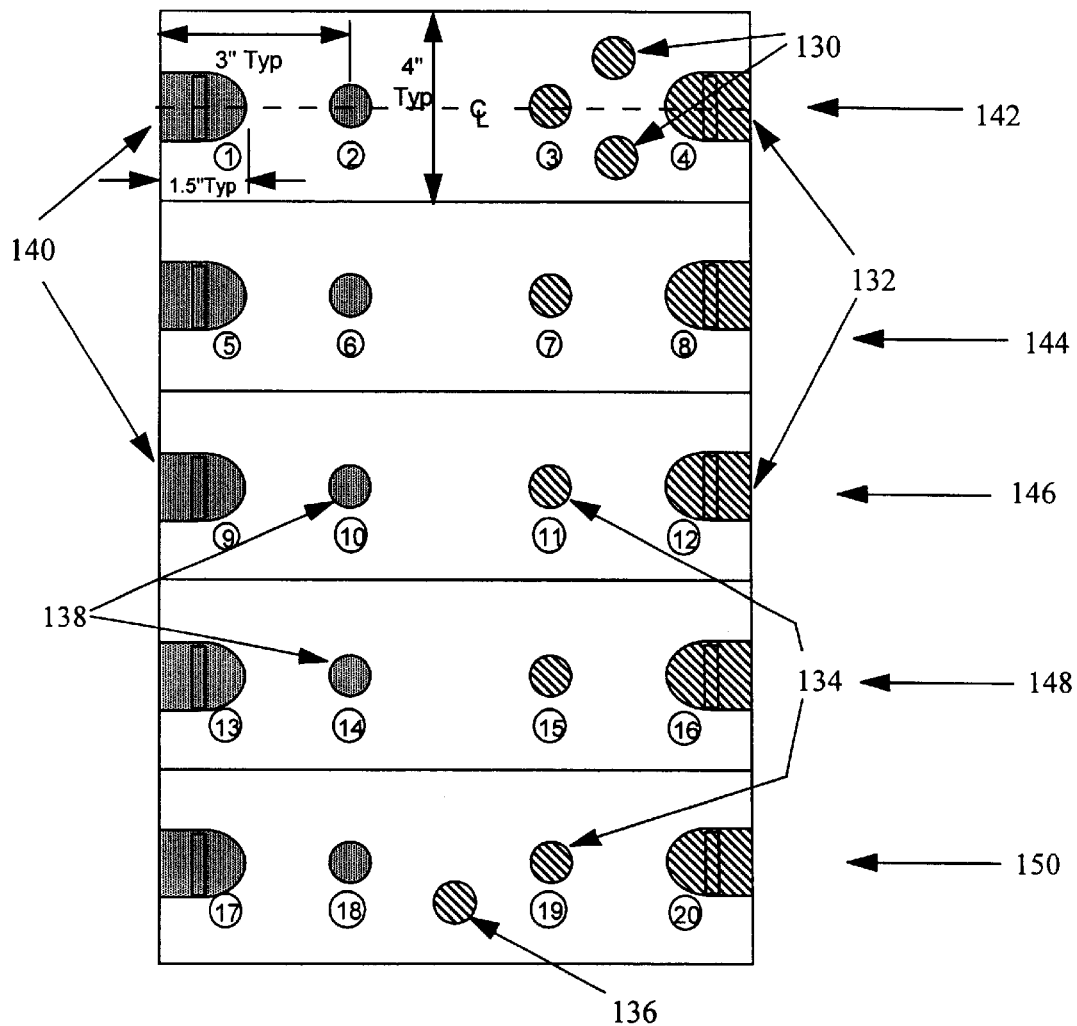
FIG. 8 shows a boron-epoxy calibration test sample structure to be inspected.

Next, a boron-epoxy calibration test sample shown in FIG. 8 was constructed with built-in flaws representing delaminations within the plies of the composite and disbonds at the aluminum skin. Thin Teflon shims 134, shown for example at the bondlines, and Teflon shims 138, shown for example between plies, were used to simulate the flaws within the composite structure. Pull tabs 132, shown for example at the bondlines, and pull tabs 140, shown for example between plies, were used at the edges of the composite which were removed after cure of the epoxy to simulate the flaws in those regions. Five four-inch wide strips of the composite with lay-ups from 8 to 72 plies were installed on a 0.07 inch thick aluminum panel to make up the entire calibration test sample that is illustrated in FIG. 8. Eight-ply strip 150 is shown next to 24-ply strip 148 which is next to 40-ply strip 146 adjacent 56-ply strip 144 which is then adjacent 72-ply strip 142.

Figure 9:
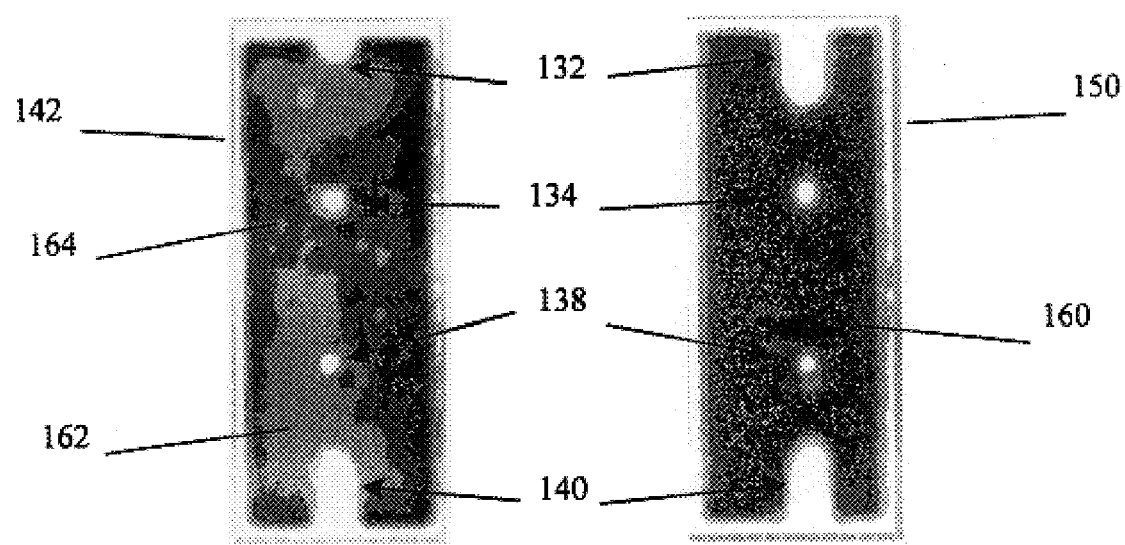
FIG. 9 shows conventional C-scan images for the 72-ply strip and 8-ply strip of FIG. 8.

To characterize the built-in flaws and assess the overall uniformity of the composite strips of the calibration test sample shown in FIG. 8, a through transmission C-scan image of the signal amplitude for each strip of the test sample was recorded using a pair of 5 megahertz, 2 inch diameter transducers. The C-scan images for 72-ply strip 142 and 8-ply strip 150 are shown in FIG. 9. Black areas, shown for example at 160, are high amplitude signals; gray areas, shown for example at 162, represent lower amplitude signals; and white areas, shown for example at 164, represent that no signal was recorded indicating an air interface. The C-scan images are normally produced in sixteen color contours but are here converted to a gray scale with less resolution between contours so that distinguishing features within the images are clearly visible in the half tone black and white print format.

In FIG. 9, pull tab region 132 at the top of 72-ply strip 142 shows an incomplete delamination in the intended area. Eight-ply strip is shown generally at 150. Non-uniform areas of the composite are also evident by the reduction of the signal amplitude recorded in regions of the normal composite lay-up. The C-scan image of 8-ply strip 150 indicates a faithful representation of the intended flaws and no nonuniform areas are observed in the remainder of the composite lay-up.

The through transmission C-scan images are helpful when interpreting the response waveforms using a pulse-echo technique in the same respective areas of the composite. For example, air interfaces, shown for example at shim inserts 134 and 138, at the intended flaw areas are confirmed by the through transmission data and the maximum change in the pulse-echo amplitude is expected at the same areas. Furthermore, other areas of the composite are identified where the pulse-echo amplitude from the composite/aluminum interface may vary due to the non-uniformity of the Anormal@ lay-up of the composite by as much as the pulse-echo amplitude would change due to a disbond. The incomplete delamination area in pull tab region 132 and 140 in 72-ply strip 142 as recorded by the through transmission C-scan can help explain the possible pulse-echo amplitude variations that will be recorded in this region.

Figure 10:
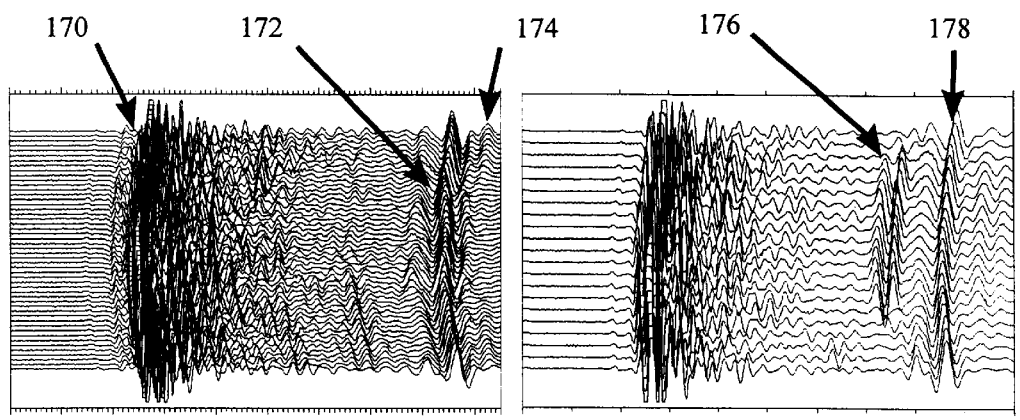
FIG. 10 shows pulse-echo response waveforms as waterfall plots of the calibration test sample shown in FIG. 8 when using a focus lens.

Next, preliminary pulse echo data for the calibration test sample shown in FIG. 8 was recorded using a 5 megahertz, 2 inch diameter, 2 inch focus transducer. Pulse-echo waveforms were recorded over the built-in flaws that were indicated by the through transmission data of FIG. 9 to have air interfaces present at the intended areas. FIG. 10 shows these pulse-echo response waveforms as waterfall plots recorded while passing the transducer over the corresponding disbond and delamination areas within the center portion of 72-ply strip 142 of the calibration test sample shown in FIG. 8.

As seen in FIG. 10, the pulse echo response for Adelamination" 176 is clearly seen in the waveforms but the pulse echo response for Adisbond@ 172 at the aluminum interface is not distinct. Aluminum skin back surface echo is shown at 174. The boron-expoxy composite front surface is shown at 170 and the composite/aluminum interface is shown at 178. No phase reversal or increase in signal amplitude for the bond-line echo is displayed at disbond 172. A slight indication of the presence of the Teflon shim is evident by the small shift of the bond-line echo to a shorter Time-Of-Flight (TOF) indicating a thinner adhesive thickness layer at the shim.

Since the presence of the Teflon shim could mask the true nature of a disbond at composite/aluminum interface 178, two additional disbond areas were fabricated in 72-ply strip 142 near the Teflon shim area. These two areas are identified in FIG. 8 at 130. The two new Adisbonds@ were created by carefully milling the aluminum base metal until very small areas of the adhesive interface were exposed. The remaining aluminum film was pulled away from the adhesive and the area was then covered with a watertight adhesive tape so that an air interface was present at the bond-line of the adhesive/aluminum interface. A similar area was also fabricated in 8-ply strip 150 as identified in FIG. 8 at 136.

Figure 11:
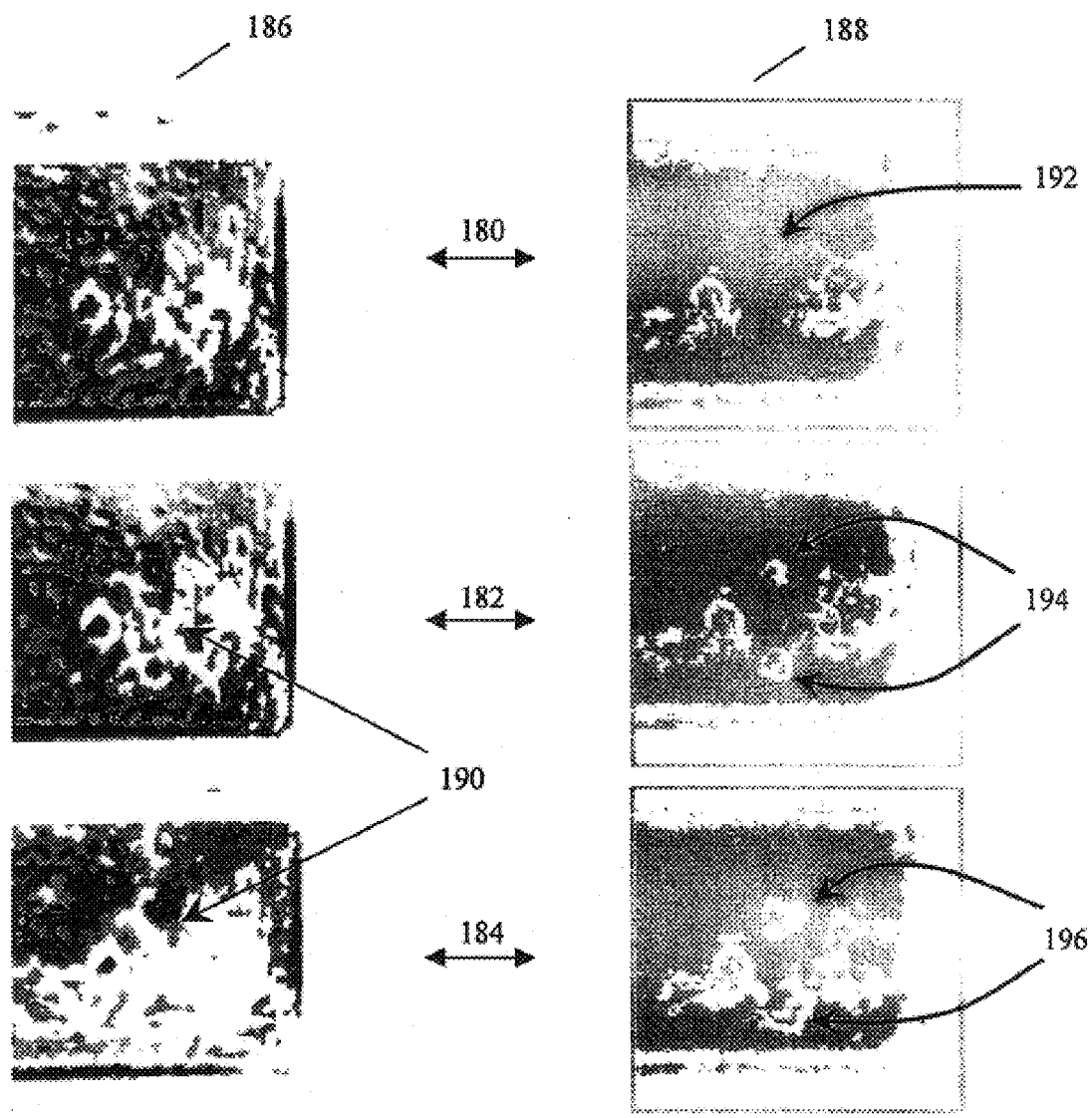
FIG. 11 shows C-scan images using a focus lens of the 72-ply strip of FIG. 8 with a range gate set for the pulse-echo waveform at the aluminum bond-line echo for scans performed before and after milling of additional disbond areas.

C-scan images of 72-ply strip 142 for a range gate set for the pulse-echo waveform at the aluminum bond-line echo 186 are shown in FIG. 11 for scans performed before and after milling of the additional Adisbon@ areas 130. For comparison, in order to show the effect of the milling process, C-scan images are also shown in FIG. 11 where the range gate was set at the back surface echo of the aluminum plate in 188. No holes, see generally 192, were detected before the aluminum skin was milled away to create new disbond areas as shown at 180. Two holes 194 were detected after ⅜ inch diameter "disbonds" were milled as shown at 182. Two holes 196 were also detected after: inch diameter "disbonds" were milled as shown at 184. These milled "disbond" areas were not detected, as shown at 190, when the image was gated on the aluminum bond-line echo 186.

The back surface echo of the aluminum plate was present for the plain aluminum plate used for the calibration test sample but for applications of the composite on an aircraft, the aluminum back surface echo will not in general be available. For aircraft, the aluminum skin can be multi-layered, backed by lap joints, stringers, tear straps etc., or it may be coated on the inside with an anti-corrosion paint layer. Any one of these conditions can interfere with the aluminum thickness echo response. For this reason, no characterization of the disbond area using the aluminum back surface echo was attempted here other than the comparison made in FIG. 11 to show the exact extent and location of the milled area in the C-scan image.

From the C-scan images of composite/aluminum bond-line echo amplitudes in FIG. 11, it was observed that the presence of a disbond at the aluminum bond-line interface was not detectable with the conventional pulse-echo technique. No significant echo amplitude change was observed at the disbond to be greater than that due to the normal lay-up of the composite using the 2 inch diameter focus transducer.

However, a noticeable change in the bond-line echo response at the disbond was observed by using the inspection device and technique of the present invention. First, refracted angles, such as those shown in FIG. 6 at 104 and 104', were calculated using L-wave velocity values that were determined in a small 72-ply boron-epoxy coupon. The L-wave velocities for different angular orientations in the coupon are listed in Table I.

TABLE I

L-wave velocity values measured in the boron-epoxy composite

| Wave Propagation Direction | L-wave Velocity (mm/:s) |
| --- | --- |
| Thickness 0 deg | 3.48 |
| 5 deg | 3.43 |
| 10 deg | 3.43 |
| 12.5 deg | 3.51 |
| 14 deg | 3.78 |
| 15 deg | 4.14 |
| Transverse 90 deg | 6.73 |

Figure 14:
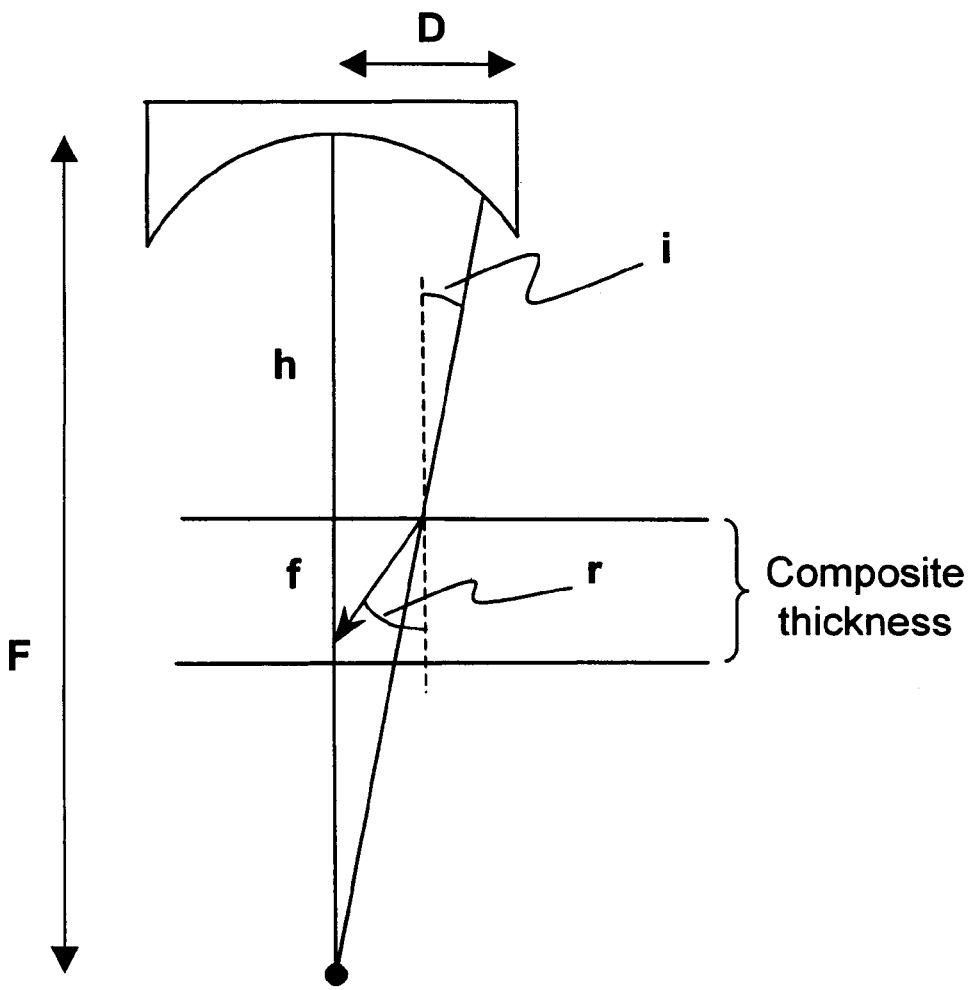
FIG. 14 shows a diagram of the parameters used in calculating L-wave velocities, refractive angles, lens curvature and focus.

These L-wave velocities were calculated at angles in the composite as follows. FIG. 14 shows a diagram of the parameters used in calculating L-wave velocities, refractive angles, lens curvature and focus. The L-wave velocity in the composite was determined by through transmission Time-Of-Flight (TOF) measurements in the principal (thickness and transverse) directions of the composite and at angles to the thickness plane of the composite. The L-wave velocity was calculated by the expression $V_L$=d/(TOF) where d is the distance or thickness of parallel sides of the sample in a given principal direction of the composite sample. The L-wave velocity in the composite at angles to the thickness plane of the composite was determined for zero degrees to 70 degrees to the normal of the thickness plane by a water immersion through transmission TOF measurement. The sample was rotated through given incident angles (i) to the path of the ultrasonic beam in water and the refractive angle (r) and L-wave velocity at that angle Vr were calculated from the expressions:

Refractive angle $r = \arctan(d \sin i / ((\Delta t\, V_w) + d \cos i))$

L-wave velocity $V_r = V_w \sin r / \sin i$ where i was the measured incident angle, d was the composite thickness, $V_w$ was the L-wave velocity in water, and $\Delta t$ was the measured TOF difference with the sample in the path of the ultrasonic beam and removed from the path of the ultrasonic beam.

The curvature of the lens and the angles of focus were calculated as follows. The curvature of the lens is given by the expression:

$R = F((n-1)/n)$ where R is the lens radius, F is the focal distance in water, $n = V/V_w$, V is the L-wave velocity in the lens material, and $V_w$ is the L-wave velocity in water.

The angle of focus and the depth of focus in the composite were determined from FIG. 14 by use of the expressions:

$f = (F-h)D/(F \tan r)$; $r = \arcsin((V° \, r/V_w) \sin i)$; $i = \arctan(D/F)$ where f was the focal distance in the composite for the water path h, D was the distance from the center line of the lens for an incident ray at angle i, and r was the refractive angle for that incident ray in the composite.

In this example, the stop was made large enough to block the center rays of the lens and small enough to provide a signal response from the composite that provided at least a 6 dB signal to noise ratio of the back surface echo from the composite-to-metal bond interface.

Next, an approximately ⅜ inch diameter, 3 inch thick cork stop, as shown for example at 92 in FIG. 6, was placed in the center of the focus lens of the transducer. By having stop 92 in the center of transducer focus lens 90, zero and low-angle ultrasonic waves shown generally at 100 in FIG. 6 were effectively blocked. Only the higher velocity outer rays 98, 98', 98", and 98'" of the ultrasonic beam waves were transmitted. Due to their refraction at 104 and 104', these rays were focused at interface 96 and enhanced the pulse-echo response.

Figure 12:
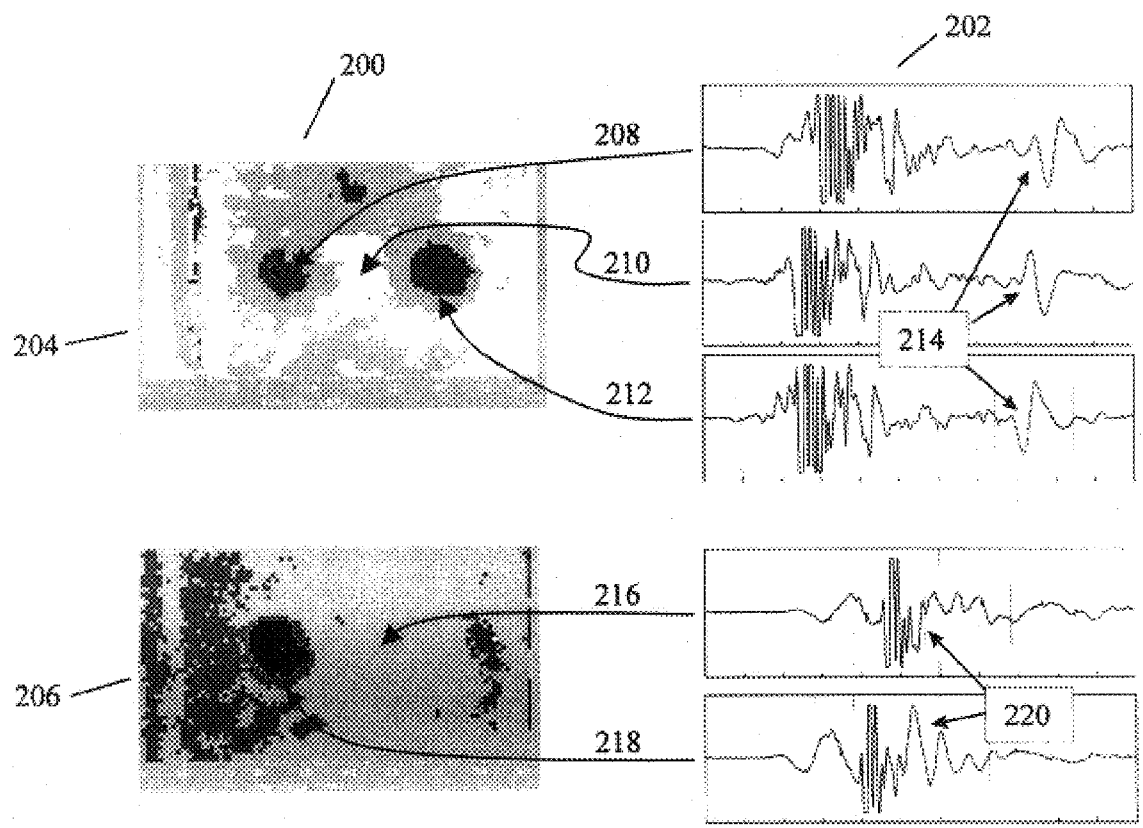
FIG. 12 shows C-scan images using a 1.0 inch diameter, 2 inch focus transducer with a stop for the 72-ply strip and 8-ply strip of the calibration test sample of FIG. 8, with the range gate set on the positive half cycle amplitudes of the bond-line echo.

The C-scan images for 72-ply strip 142 and 8-ply strip 150 of the calibration test sample of FIG. 8 are shown in FIG. 12 at 200, where the range gate was set on the positive half cycle amplitudes of the bond-line echo using the modified 1.0 inch diameter, 2 inch focus transducer with the stop. Also shown in FIG. 12 are corresponding A-scan waveforms 202 recorded at the locations of the disbond and at a "normal" bonded area. The scans for 72-ply strip 142 with the two new milled disbond areas are shown generally at 204. The scans for 8-ply strip 150 with the one new milled disbond area is shown generally at 206. Disbonds are shown at 208, 212, and 218. Bonded areas are shown at 210 and 216. A-scan waveforms 202 show the apparent phase reversal of bond-line echos 214 and 220 at disbonded areas.

Figure 13:
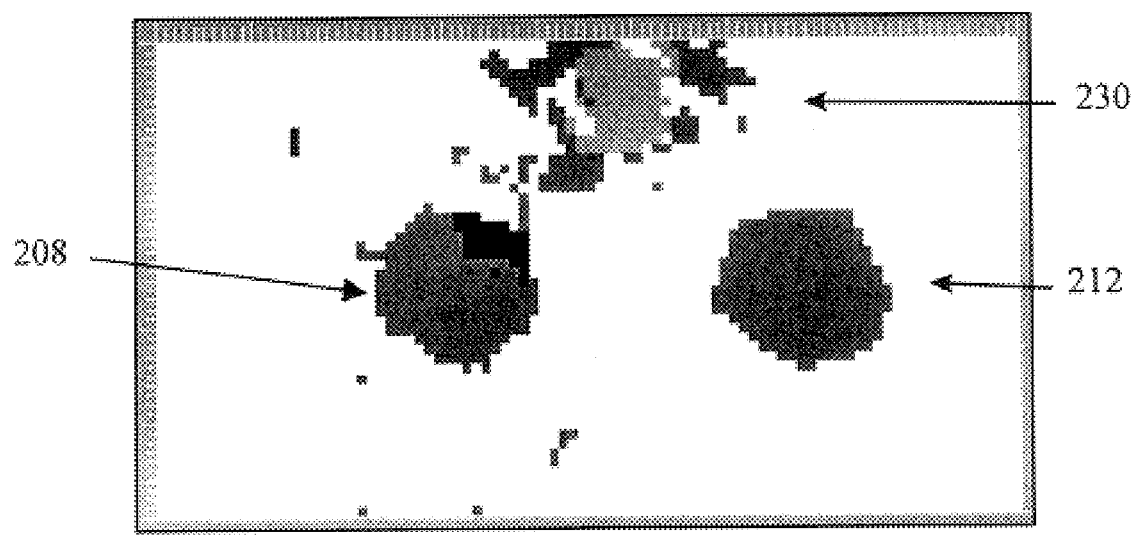
FIG. 13 shows an unambiguous C-scan image of the disbanded areas of the 72-ply strip of FIG. 12 by setting a TOF range gate for only negative cycles of the echoes.

The echo response using the modified focus transducer with the stop clearly displays an apparent phase reversal and an apparent increase of the positive half cycles of the echo. By setting a TOF gate for only negative cycles of the echoes for 72-ply strip 142 shown generally at 204 in FIG. 12, a robust and unambiguous C-scan image of disbanded areas 208 and 212 of FIG. 12 in the boron-epoxy/aluminum interface are produced as illustrated in FIG. 13. The disbond area at Teflon shim 230 is also displayed in FIG. 13.

The results presented in this example were recorded by an ultrasonic data acquisition system with the samples placed in a water immersion tank. The modified focus transducer with stop described here can be deployed in portable ultrasonic data acquisition and display systems. For the portable system, the immersion focus transducer can be placed into the body of the weeper or dripless bubbler transducer holder. In this example, the weeper transducer holder was used, and the water cavity therein was machined into a conical shape to accommodate the 1.0 inch diameter transducer with no problems.

This example demonstrated that a pulse-echo technique was developed that produces a significant change in the pulse-echo response from a boron-epoxy/aluminum skin interface where disbonds are present. As a result, ultrasonic inspections of boron-epoxy doublers can be conducted where Time-OF-Flight C-scan images can be produced that show unambiguously the disbanded areas at the aluminum skin interface. The preceding example can be repeated with similar success by substituting the generically or specifically described operating conditions of this invention for those used in the preceding example.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An apparatus for performing ultrasonic inspection of a structure, said apparatus comprising:
   a transducer adapted to generate ultrasonic waves and transmit them generally according to a prevailing direction creating a trace whereby a two-dimensional area transecting said waves is described corresponding to the trace of said waves; and a stop proximate said transducer and positioned centrally within said two-dimensional area, wherein some of the ultrasonic waves generated by said transducer pass unobstructed by said stop into said structure causing therein the formation of cohesively converging L-waves within said structure.

2. The apparatus of claim 1 further comprising a focus lens.

3. The apparatus of claim 2 wherein said focus lens comprises a material conductive of ultrasonic waves.

4. The apparatus of claim 2 wherein said focus lens comprises a material refractive of ultrasonic waves.

5. The apparatus of claim 2 wherein said focus lens comprises a focus lens defining a radius of curvature such that signal waves transmitted by said transducer are focused upon a selected area of the structure.

6. The apparatus of claim 1 further comprising a scanning system housing said transducer.

7. The apparatus of claim 1 further comprising a couplant between said transducer and the structure.

8. The apparatus of claim 1 further comprising a scanning shoe between said transducer and the structure.

9. The apparatus of claim 1 wherein said stop comprises an ultrasonic-attenuating material.

10. The apparatus of claim 1 wherein said stop comprises a diameter such that selected ultrasonic waves emitted from the transducer are prevented from passing through a central portion of said region describing a two-dimensional area, and are further prevented from generating L-waves within the structure.

11. The apparatus of claim 1 wherein said transducer comprises an ultrasonic transducer.

12. The apparatus of claim 11 wherein said transducer comprises an ultrasonic transducer having a diameter of at least approximately 0.5 inches.

13. The apparatus of claim 12 wherein said ultrasonic transducer has a diameter of approximately 1.0 inches.

14. The apparatus of claim 11 wherein said ultrasonic transducer operates between approximately 0.1 and approximately 25 megahertz.

15. The apparatus of claim 14 wherein said ultrasonic transducer operates at approximately 5 megahertz.

16. The apparatus of claim 1 wherein said stop comprises a cork.

17. The apparatus of claim 16 wherein said stop comprises a cylindrical cork button having a diameter of approximately 0.5 inches and a thickness of approximately 0.25 inches.

18. A method of inspecting a structure having physical properties that allow for production of L-waves therein using an apparatus comprising at least one ultrasonic transducer for producing and receiving an ultrasonic signal, a focus lens coupled to the transducer for focusing the ultrasonic signal whereby paths of ultrasonic waves comprising the produced ultrasonic signal create a trace, and a stop located near the lens for blocking the ultrasonic signal, the method comprising the steps of:

a) coupling the transducer output to the structure;

b) blocking selected wave components positioned centrally within the trace of the ultrasonic signal produced by the transducer;

c) transmitting selected wave components positioned peripherally within the trace of the ultrasonic signal produced by the transducer through the structure; and d) receiving a reflected ultrasonic signal from the structure.

19. The method of claim 18 further comprising the step of focusing the ultrasonic signal from the transducer upon a selected area of the structure to be inspected.

20. The method of claim 18 further comprising the step of using a scanning shoe to increase the distance traveled by the ultrasonic signal between the transducer and structure.

21. The method of claim 18 further comprising the step of producing an image of the received ultrasonic signal revealing defects within the structure.

22. The method of claim 21 further comprising the step of gating the image to reveal the reflected ultrasonic signal at selected depths.

23. The method of claim 18 wherein said structure is selected from the group consisting of anisotropic structures, composite structures and combinations thereof.

* * * * *